US00PP22717P3

(12) United States Plant Patent
Vinson et al.

(10) Patent No.: US PP22,717 P3
(45) Date of Patent: May 8, 2012

(54) STRAWBERRY PLANT NAMED 'VIVA PATRICIA'

(50) Latin Name: ***Fragaria×ananassa* Duch.**
Varietal Denomination: Viva Patricia

(75) Inventors: Peter Edward Vinson, Faversham (GB); Simon Peter Warren, Faversham (GB)

(73) Assignee: Edward Vinson Limited, Kent (GB)

( * ) Notice: Subject to any disclaimer, the term of this patent is extended or adjusted under 35 U.S.C. 154(b) by 189 days.

(21) Appl. No.: 12/591,173

(22) Filed: Nov. 12, 2009

(65) Prior Publication Data

US 2010/0138966 P1 Jun. 3, 2010

(30) Foreign Application Priority Data

Dec. 1, 2008 (EP) ..... 2008/2790

(51) Int. Cl.
*A01H 5/00* (2006.01)

(52) U.S. Cl. ..... Plt./208

(58) Field of Classification Search ..... Plt./208
See application file for complete search history.

(56) References Cited

U.S. PATENT DOCUMENTS

PP8,708 P * 5/1994 Voth et al. ..... Plt./209
PP11,555 P * 10/2000 Leis et al. ..... Plt./208
PP16,571 P3 * 5/2006 Weber et al. ..... Plt./208
PP16,766 P2 * 7/2006 Herrington et al. ..... Plt./208
PP18,340 P3 * 12/2007 Jamieson ..... Plt./208

OTHER PUBLICATIONS

Anonymous. "New Strawberry bred for Britain" Horticulture Week. Apr. 17, 2009. Available at: http://www.hortweek.com/news/898453/New-strawberry-bred-Britain/.*
Barker, Michael. "New strawberry Viva Patricia hits UK shelves" thegrocer. Apr. 17, 2009. Available at: http://thegrocer.co.uk/articles.aspx?page=articles&ID=199173.*
UPOV ROM GTITM Computer Database, GTI Jouve Retrieval Software 2011/01 "QZ" Citation for 'Viva Patricia'.*
UPOV ROM GTITM Computer Database, GTI Jouve Retrieval Software 2011/01 "AU" Citation for 'Viva Patricia'.*
UPOV ROM GTITM Computer Database GTI Jouve Retrieval Software 2011/01 "ES" Citation for 'Viva Patricia'.*

* cited by examiner

*Primary Examiner* — Wendy C Haas
(74) *Attorney, Agent, or Firm* — Rosenberg, Klein & Lee

(57) ABSTRACT

This invention relates to a new and distinctive short-day cultivar, designated as 'Viva Patricia', primarily adapted to the growing conditions in Spain. This short-day (Mediterranean) cultivar is primarily characterized by an upright and dense growth habit, a large fruit size having superior uniformity, a primarily conical shaped berry exhibiting a glossy bright red appearance, a significantly better flavored and aromatic berry providing a more pleasant eating experience, a firmer fruit skin, an increased number of flowers and fruits per truss, a very moderate petiole pubescence, and an early to mid-season production with substantial yields and excellent commercial ratings.

18 Drawing Sheets

Figure 1:
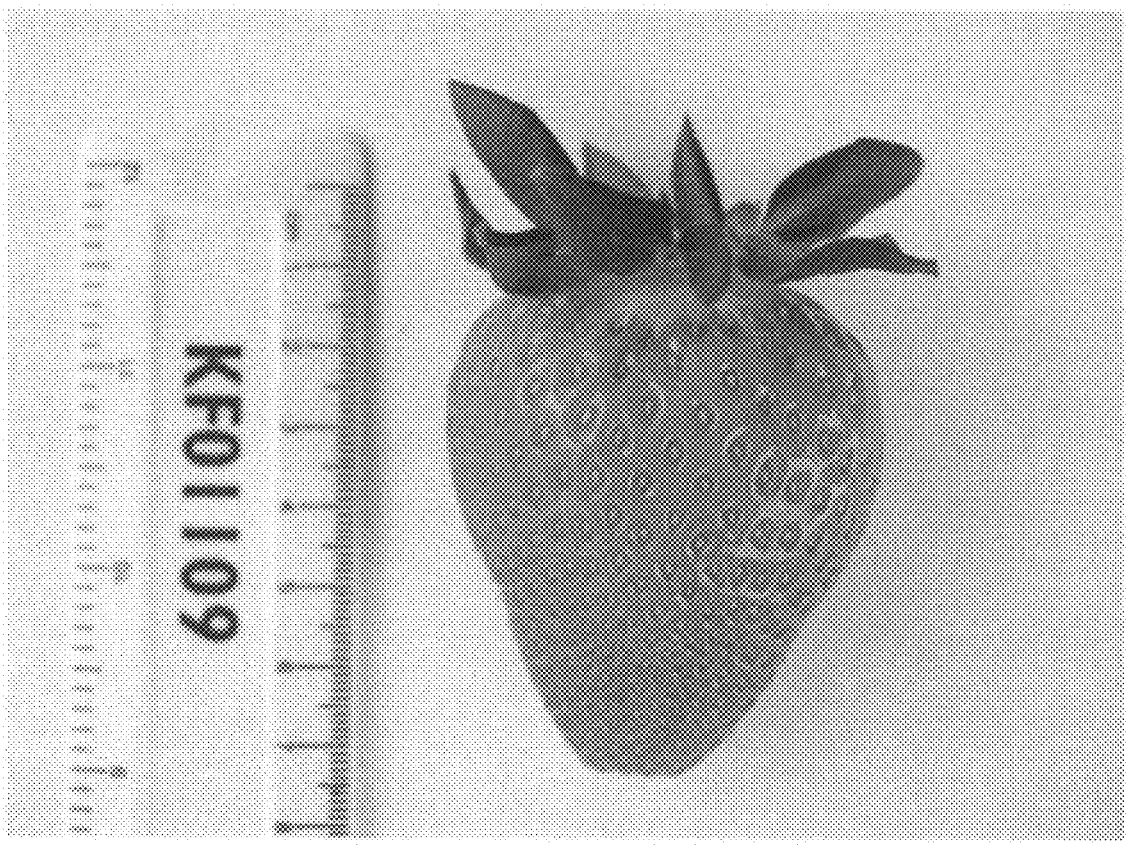

Genus and species: *Fragaria×ananassa* Duch.
Cultivar denomination: 'Viva Patricia'.

PRIORITY CLAIM

This application claims priority under 35 U.S.C. § 119(f) of application number 2008/2790 filed on 1 Dec. 2008 at the European Community Plant Variety Office (CPVO).

BACKGROUND OF THE INVENTION

The new and distinct cultivar of strawberry originated from a controlled cross performed in a glasshouse in Kent, UK being one seedling from 10,000, which were transferred to Cartaya, Huelva, Spain in October 2004, as part of the ongoing breeding program in that country. The cross was made between the agricultural selections S03AC11 (unpatented) and S02AG4 (unpatented) in 2004.

SUMMARY OF THE INVENTION

The present invention relates to a new and distinct short day (Mediterranean) strawberry cultivar designated as 'Viva Patricia.' The cultivar is botanically known as *Fragaria×ananassa* Duch. Under growing conditions in Spain, this short day (Mediterranean) cultivar has shown improvements over the varieties 'Sabrosa' (U.S. Plant Pat. No. 16,558) and 'Camarosa' (U.S. Plant Pat. No. 8,708). Improvements include, but are not limited to, improved shelf life, improved flavor and Brix levels, and superior eating quality.

The female parent, S03AC11, is a Mediterranean short day cultivar that was selected in Spain in 2003. S03AC11 exhibits a moderate crop of medium sized berries having high sugars, good flavor, and a pleasant aroma, but expressing a soft skin. S03AC11 was selected as a parent for its even shape and its flavor characteristics. S03AC11 has medium vigor and is a compact plant; however, this cultivar does not express sufficiently desirable characteristics to render it a commercially viable cultivar.

The male parent, S02AG4, is a Mediterranean short day cultivar that was selected in Spain in 2002. When grown in Spain, S02AG4 crops from February until the end of May. S02AG4 was selected as a parent because the cultivar exhibits a large fruit having a pale color. As the male parent expresses a low yield, a soft skin, and a bland flavor, this cultivar would not meet the specifications required for commercialization.

Both parents, SO3AC11 and S02AG4 are hybrids of *Fragaria×ananassa* Duch and were selected in a Mediterranean breeding field located in Cartaya, Spain as part of an ongoing breeding program in that country. Accordingly, the cultivar 'Viva Patricia' is of the species *Fragaria×ananassa* Duch.

The seedling, which fruited in the spring of 2005 at the seedling field located in Cartaya, Spain, was originally designated S05VS38 and subsequently named 'Viva Patricia' for introduction. 'Viva Patricia' was selected because the cultivar produces a high yield of extremely high quality and good sized fruit. Additionally, the cultivar exhibits excellent firmness and flavor characteristics.

'Viva Patricia' was trialed in trial plots in Cartaya, Spain during the years 2006, 2007, 2008 and 2009. During the period of trials 'Viva Patricia' was reproduced asexually for four (4) successive years. For each trial year, asexual propagation of 'Viva Patricia' was by means of stolons (runners) and took place at the glasshouse facility located in Kent, United Kingdom. Additionally, during the year 2007, a limited number of 'Viva Patricia' plants were reproduced asexually by stolons at a propagation facility located in Egham, Surrey, United Kingdom.

During 2008, a quantity of plants were produced asexually by stolons at a high elevation nursery in the north of Spain using mother plants which had been produced by tissue culture. In all four (4) generations, plants were observed for trueness to type during the fruiting phase with no abnormalities being observed. This propagation demonstrated no obvious abnormalities in these plants. All propagules of 'Viva Patricia' have been observed to be true to type in that during all asexual multiplication, the vegetative and fruit characteristics of the original plant have been maintained.

The new cultivar is primarily adapted to the climate and growing conditions of southern Spain and other regions of similar climate and day length. These regions provide the necessary conditions required for it to produce a strong vigorous plant and to produce fruit in the spring harvest season from February to May, depending on location.

The following list of traits, in combination, defines the new cultivar as a unique cultivar distinguishable from other commercial varieties in the region:

- vigorous and dense growth habit;
- large fruit size;
- primarily conical berries, with occasional wedge shaped berries, exhibiting a glossy bright red appearance;
- flavorful berries with good aroma and high Brix levels;
- firm fruit skin, moderate flesh firmness and pleasant eating experience;
- increased total yield due to larger fruit size and higher fruit numbers;
- very moderate petiole pubescence; and
- mid-season production with substantial yields.

BRIEF DESCRIPTION OF THE PHOTOGRAPHS

The accompanying color photographs show typical specimens of the new cultivar, designated at various stages of development as nearly true as is possible to make in color reproductions. The depicted plant and plant parts were from the 2009 harvest season, approximately five (5) months after planting.

FIG. 1 Typical fully developed primary fruit, measured in length (cm).

Figure 2:
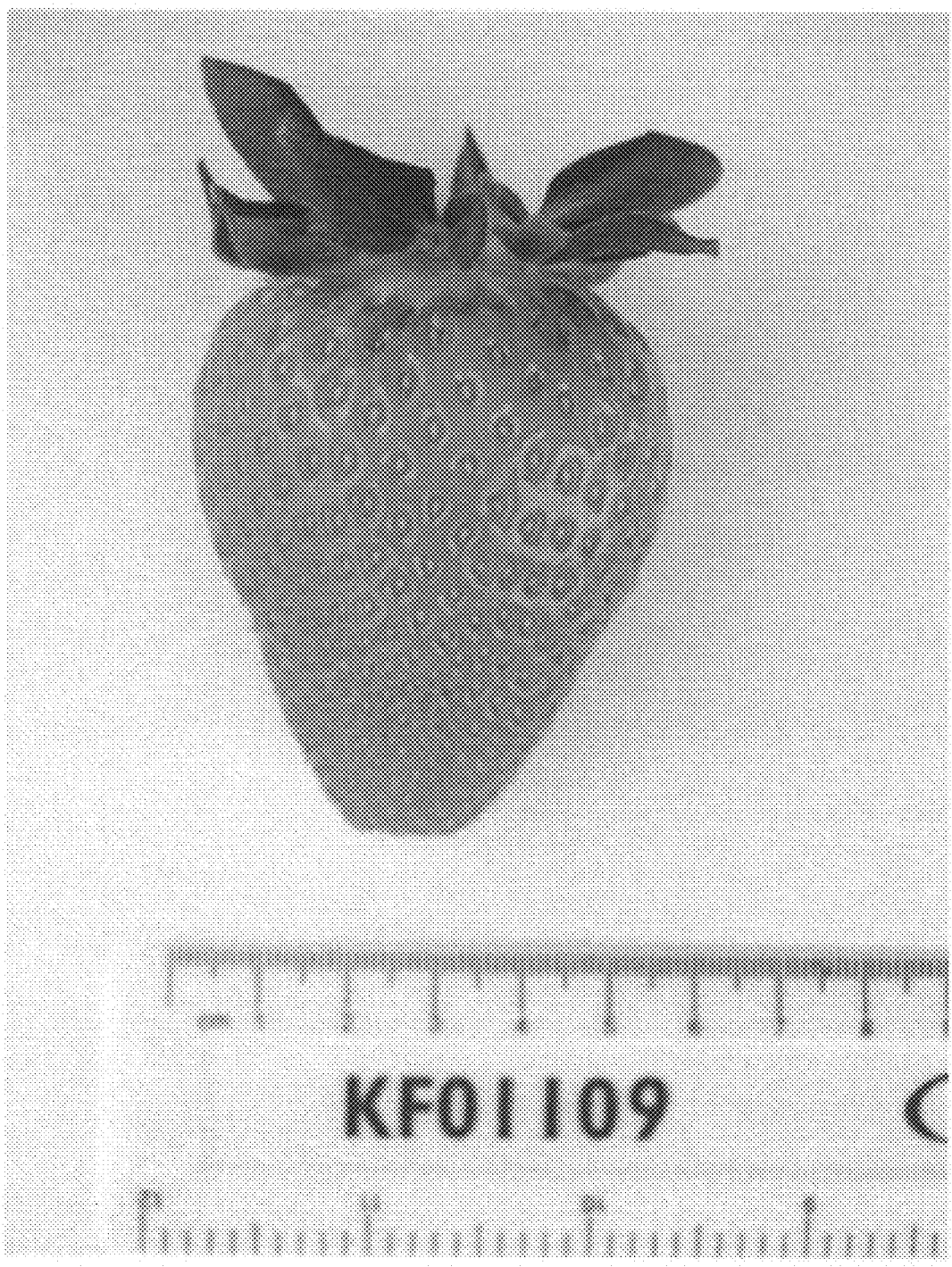

FIG. 2 Typical fully developed primary fruit, measured in width (cm).

Figure 3:
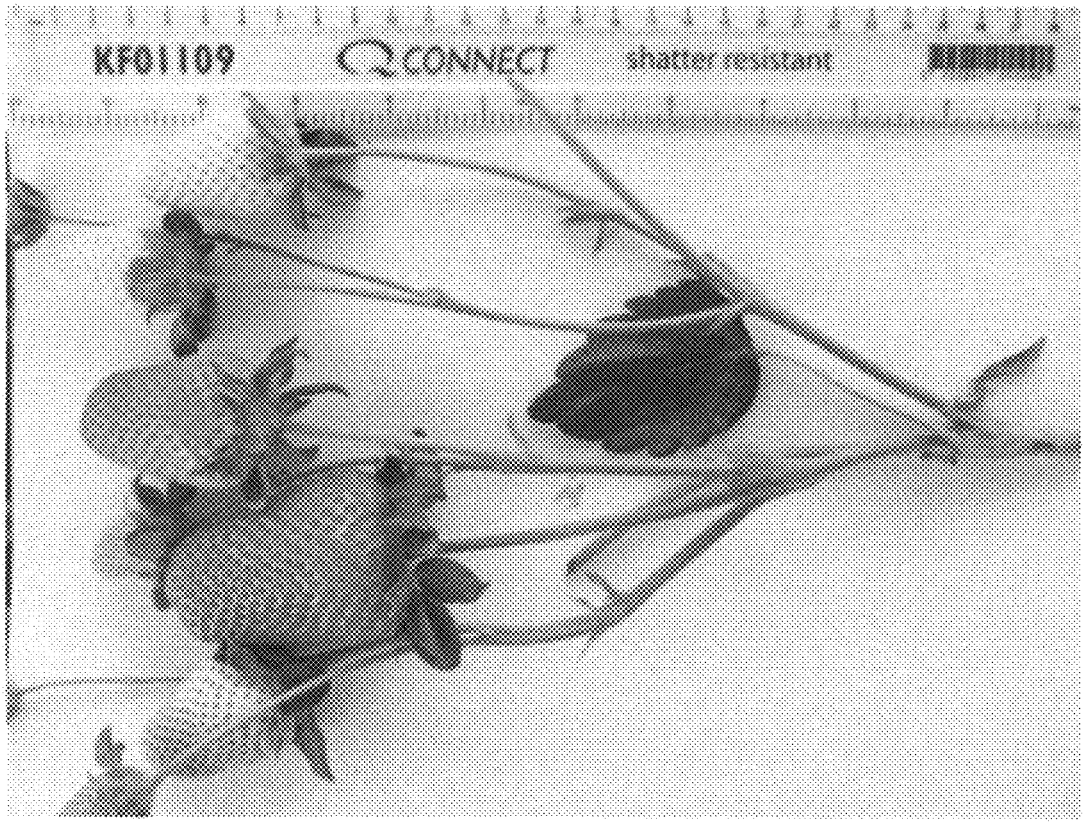

FIG. 3 Typical mid-season fruiting truss.

Figure 4:
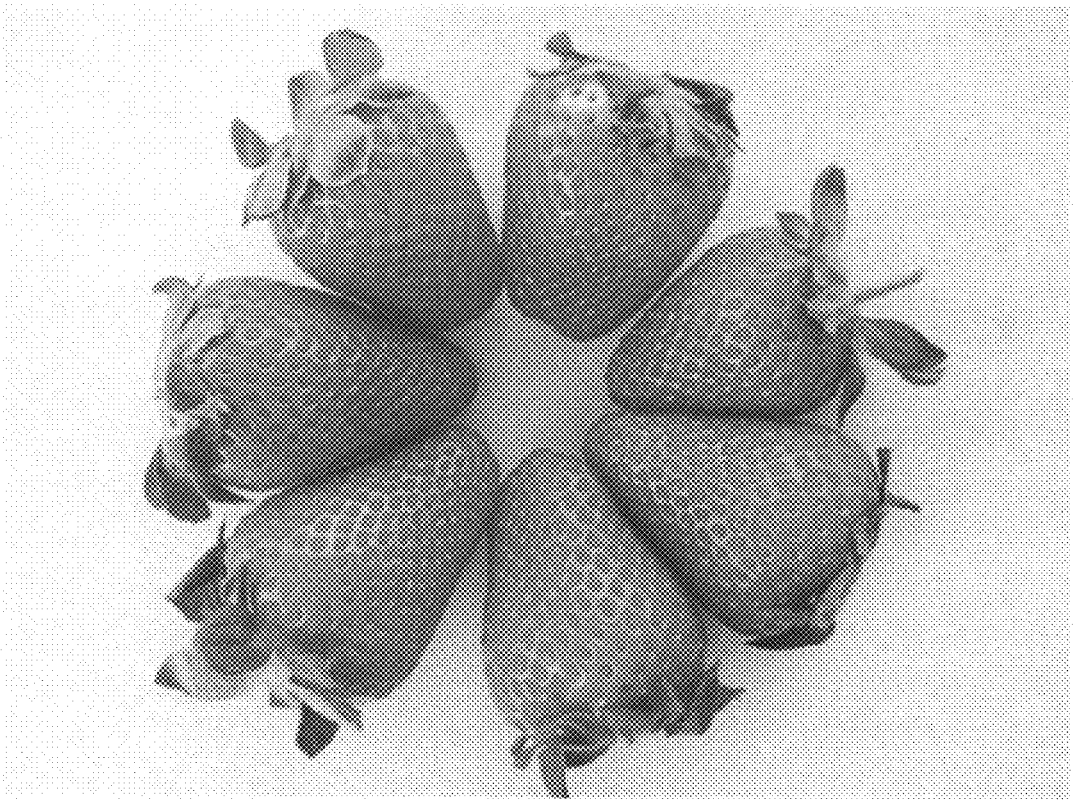

FIG. 4 A selection of large primary fruits, mostly conical in shape, with the occasionally wedge shaped fruit.

Figure 5:
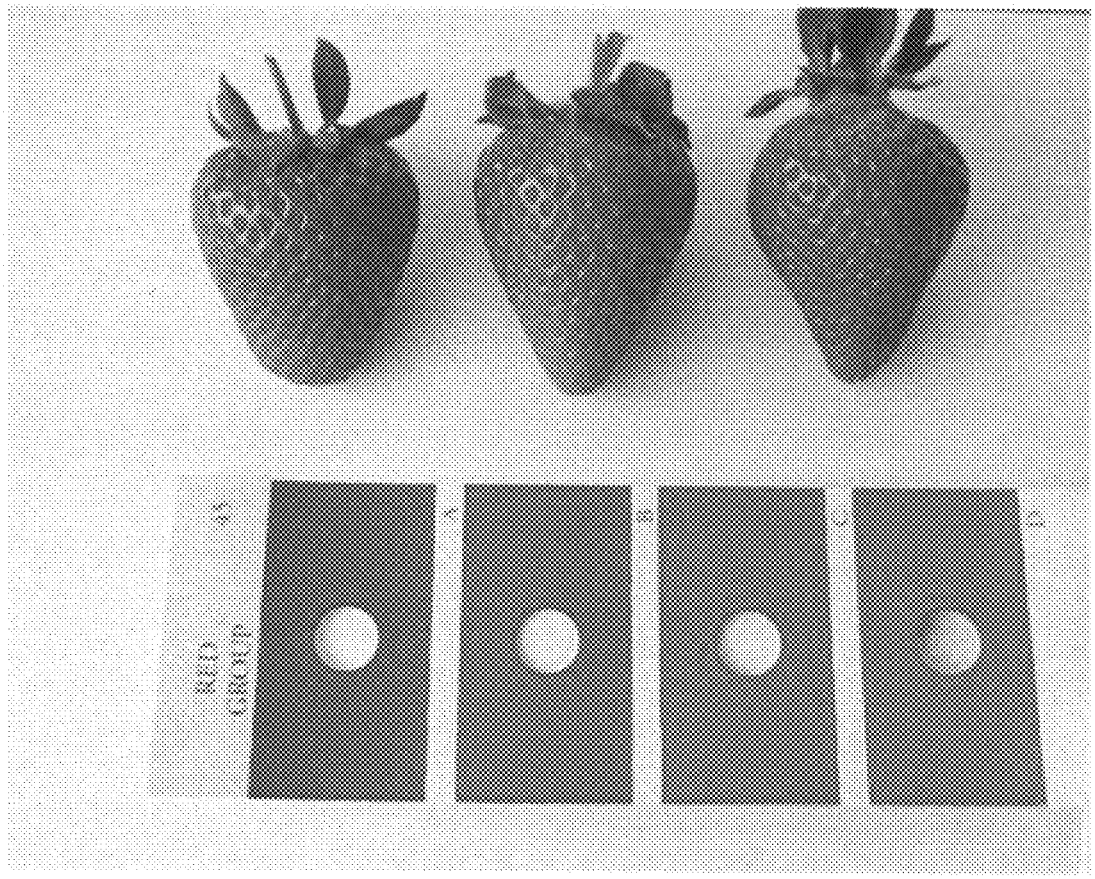

FIG. 5 'Viva Patricia' fruit skin color identified using The 1995 Royal Horticultural Society Colour Chart (45A or 45B depending on maturity).

Figure 6:
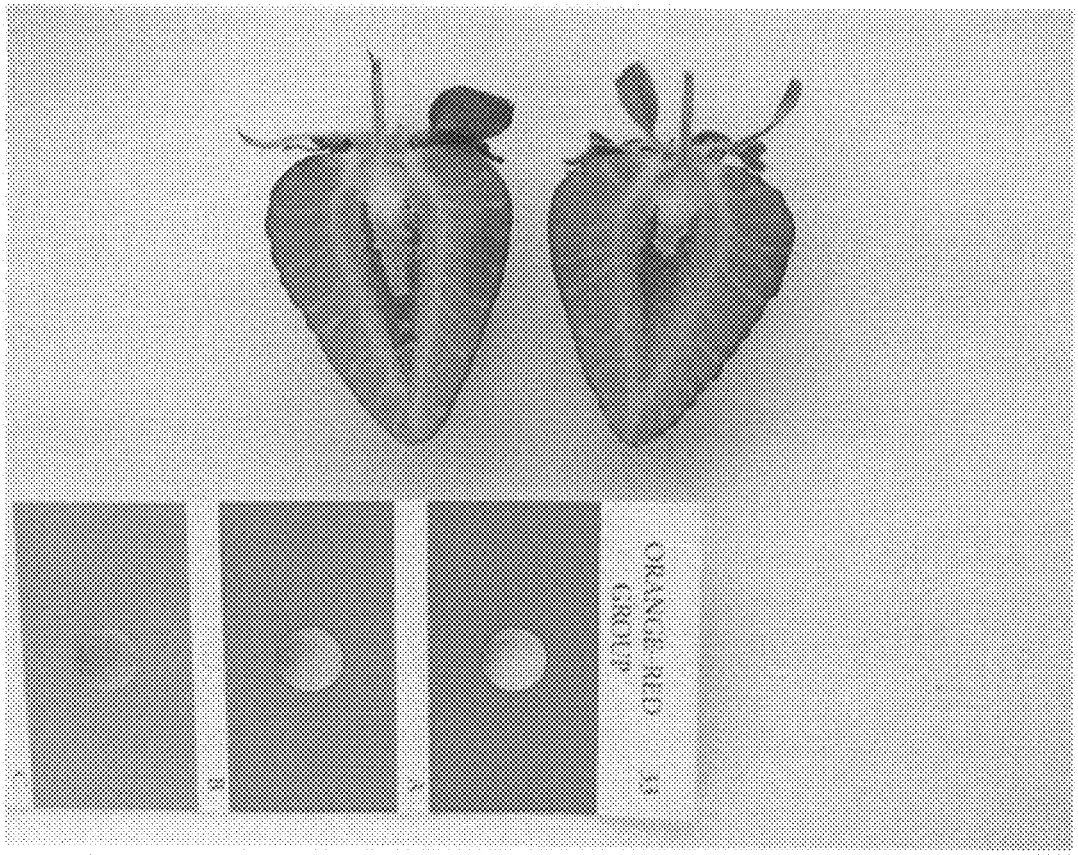

FIG. 6 Typical 'Viva Patricia' fruit interior flesh coloration near the outside fruit surface identified using The 1995 Royal Horticultural Society Colour Chart (33A).

Figure 7:
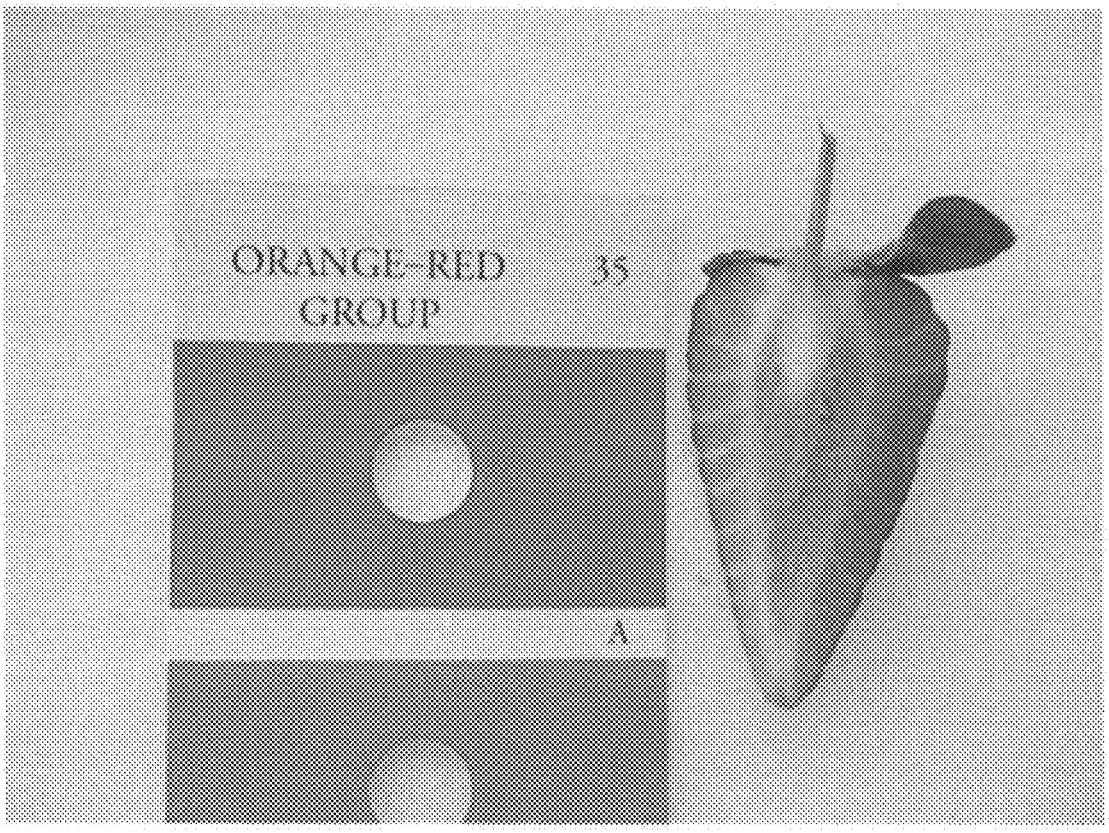

FIG. 7 Typical 'Viva Patricia' fruit inner core coloration identified using The 1995 Royal Horticultural Society Colour Chart (35A).

Figure 8:
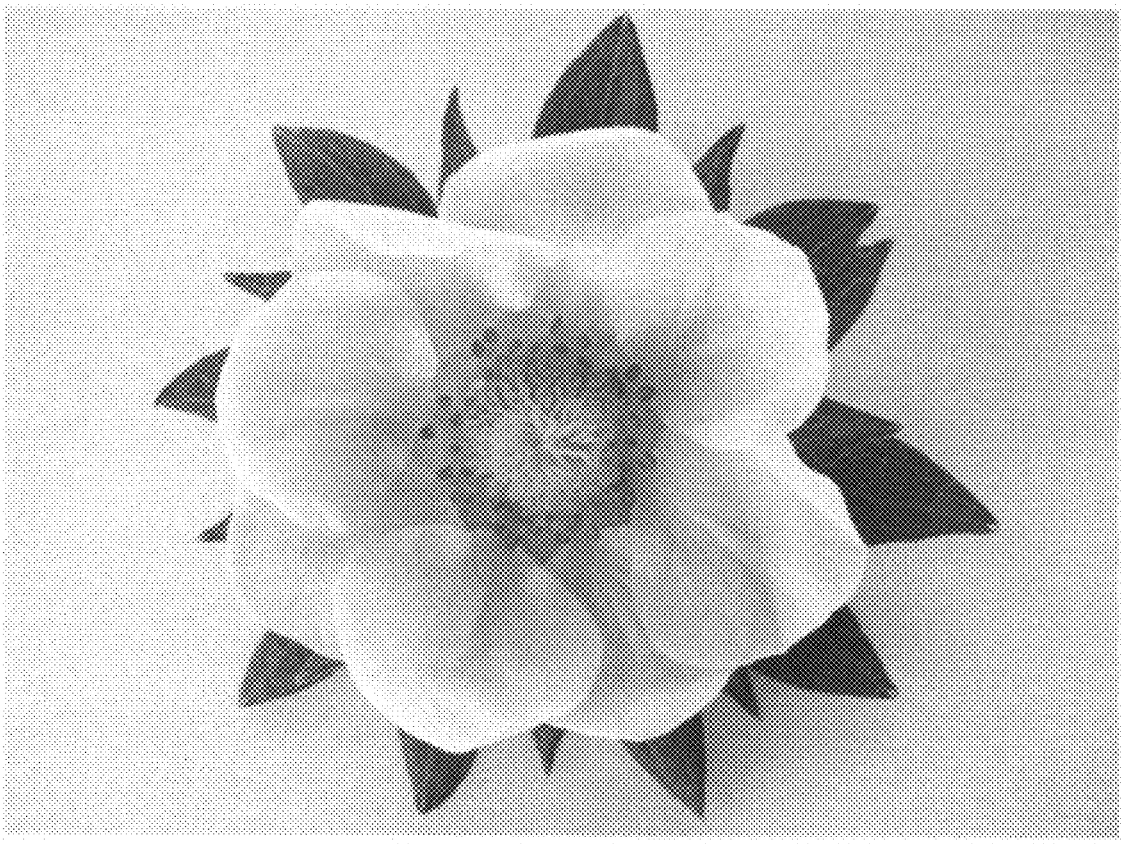

FIG. 8 A 'Viva Patricia' flower with visible corolla (petals, stamens, and ovary).

Figure 9:
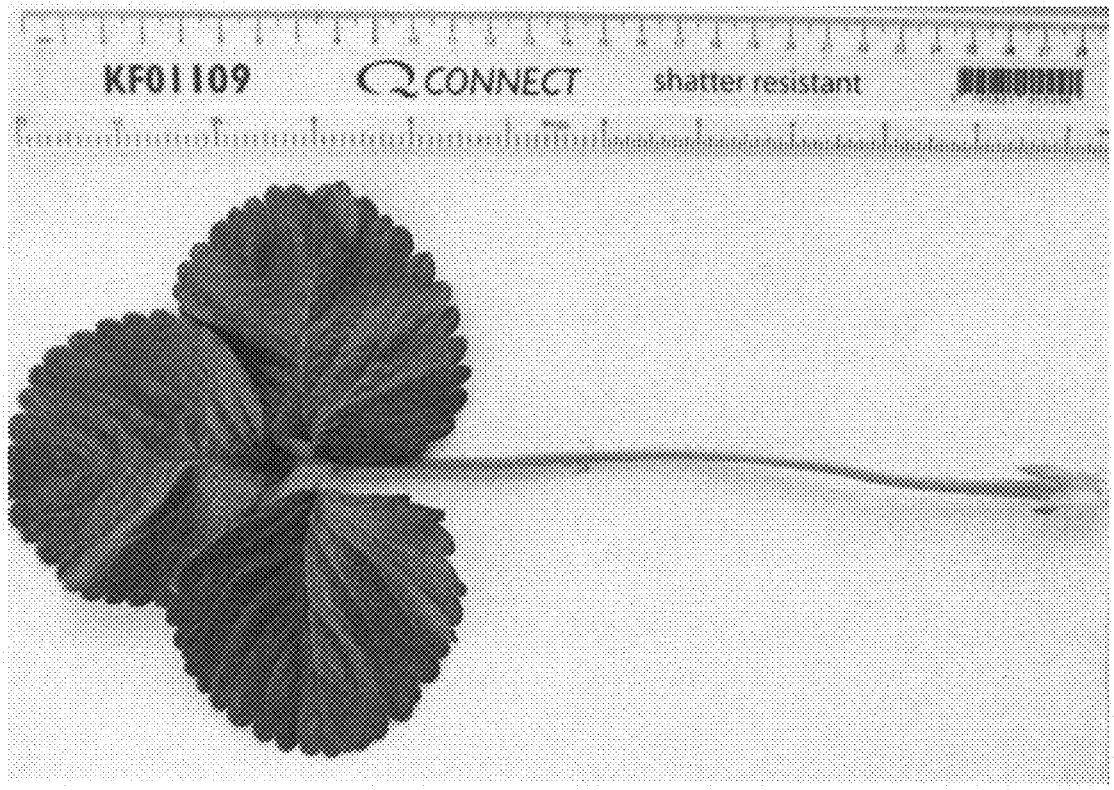

FIG. 9 A typical mature leaf with attached petiole and leafy stipule at the base of the petiole, measured in length and having slightly pointed to slightly rounded serrations and channel-like venations.

Figure 10:
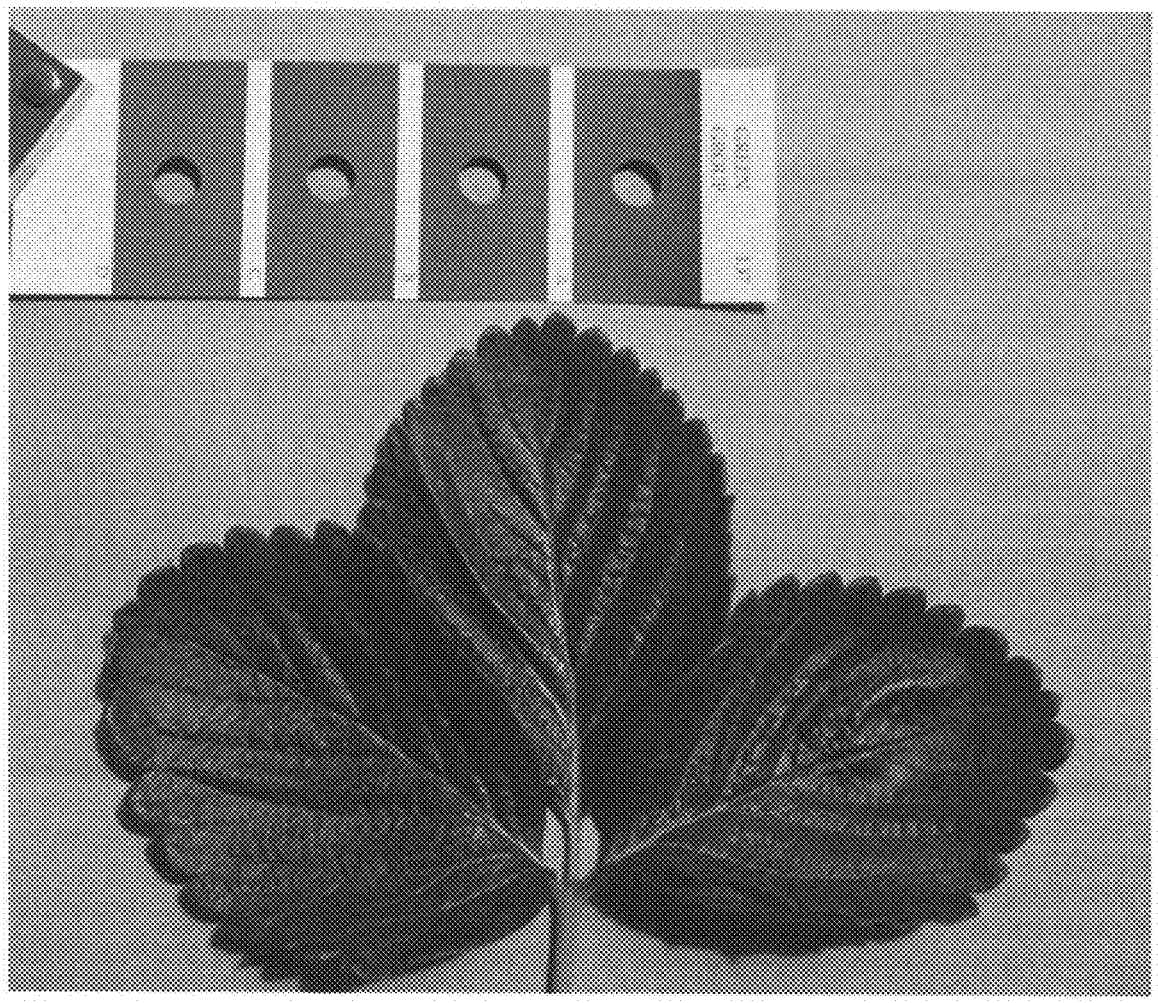

FIG. 10 Upper leaf surface color identification of a fully expanded 'Viva Patricia' leaf using The 1995 Royal Horticultural Society Colour Chart (137A).

Figure 11:
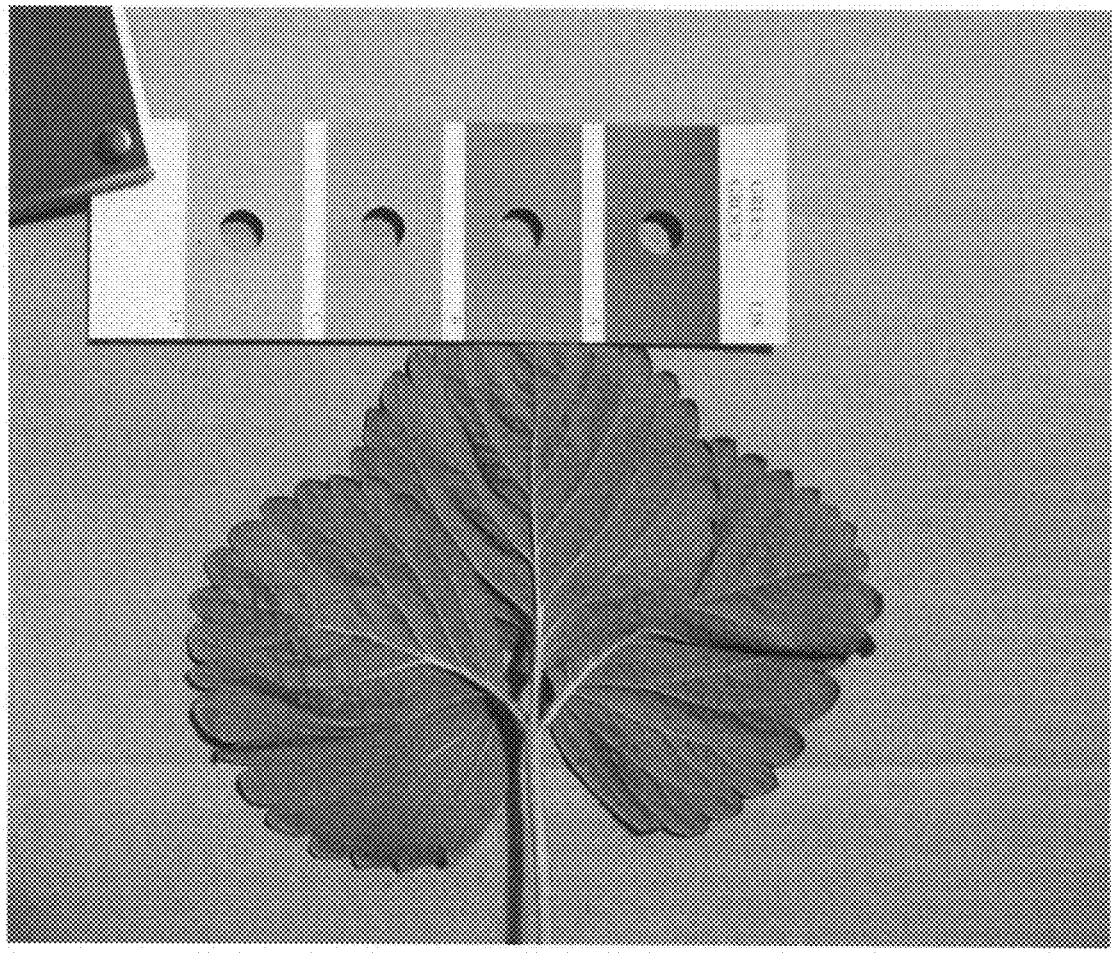

FIG. 11 Lower leaf surface color identification of a fully expanded 'Viva Patricia' leaf using The 1995 Royal Horticultural Society Colour Chart (138B).

Figure 12:
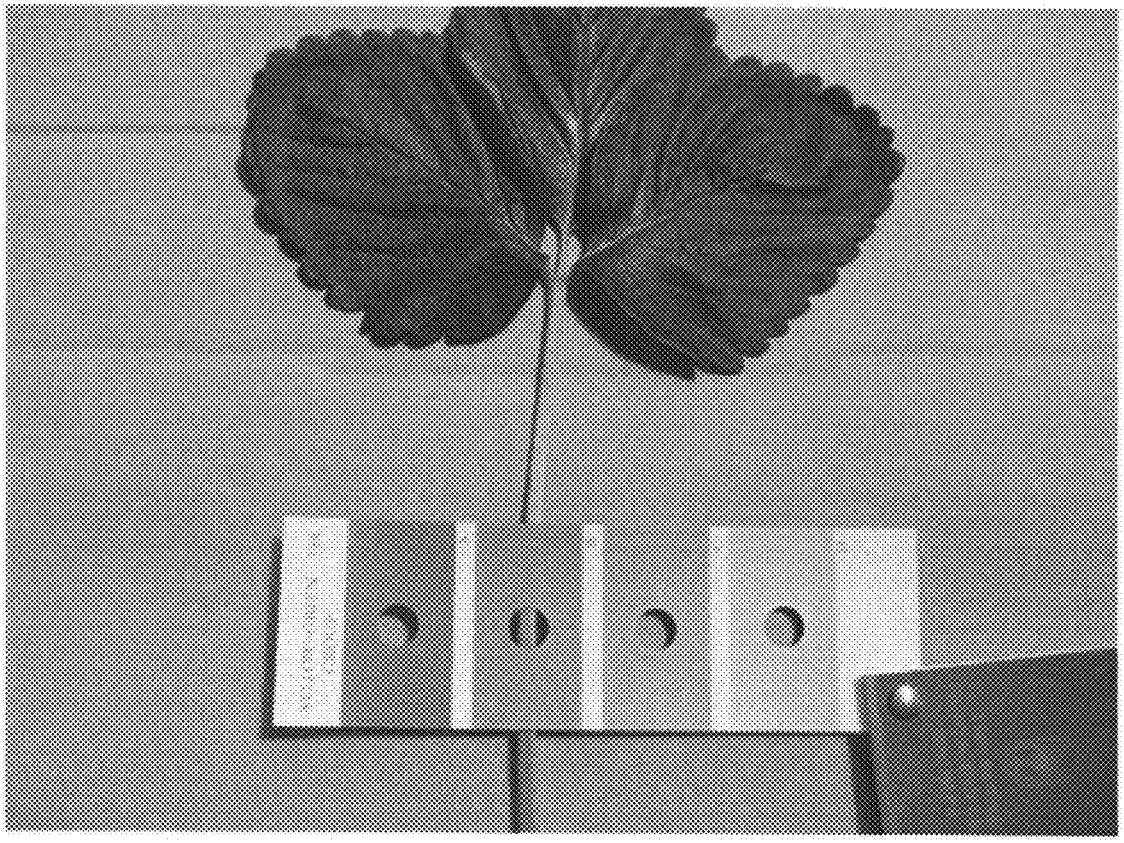

FIG. 12 Petiole color identification using The 1995 Royal Horticultural Society Colour Chart (144B).

Figure 13:
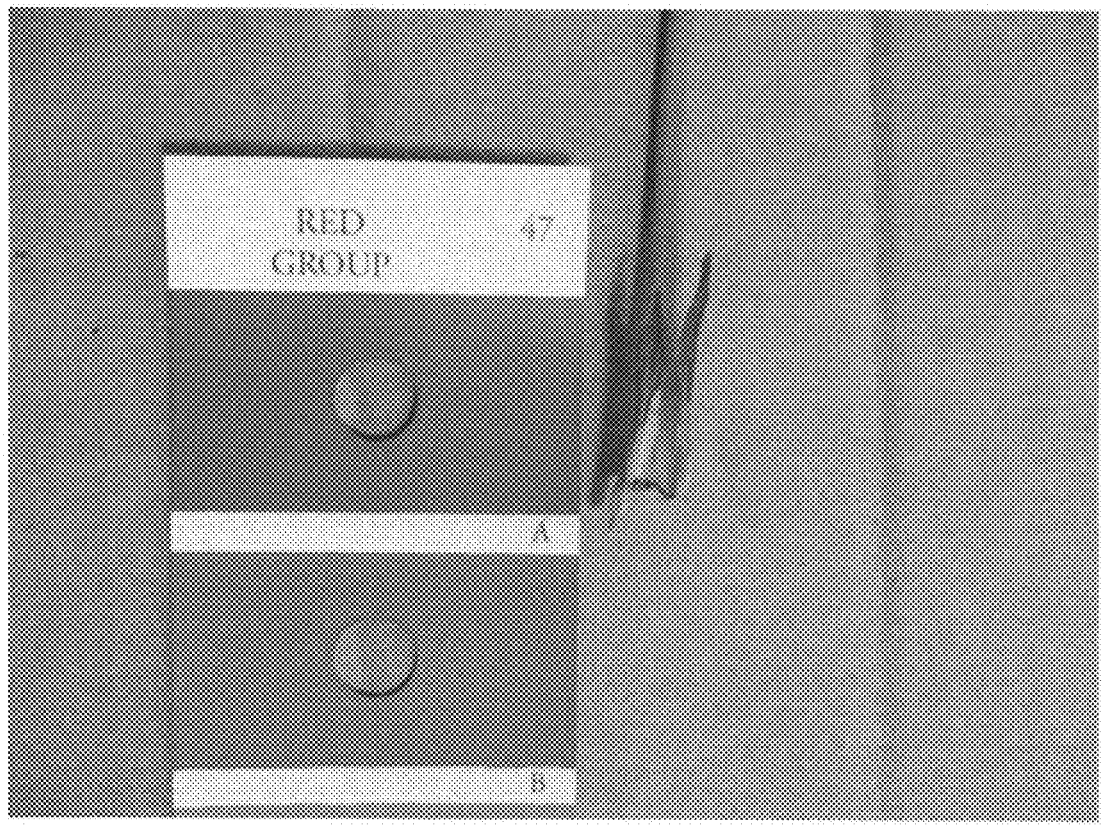

FIG. 13 Mature stipule color identification using The 1995 Royal Horticultural Society Colour Chart (47A).

Figure 14:
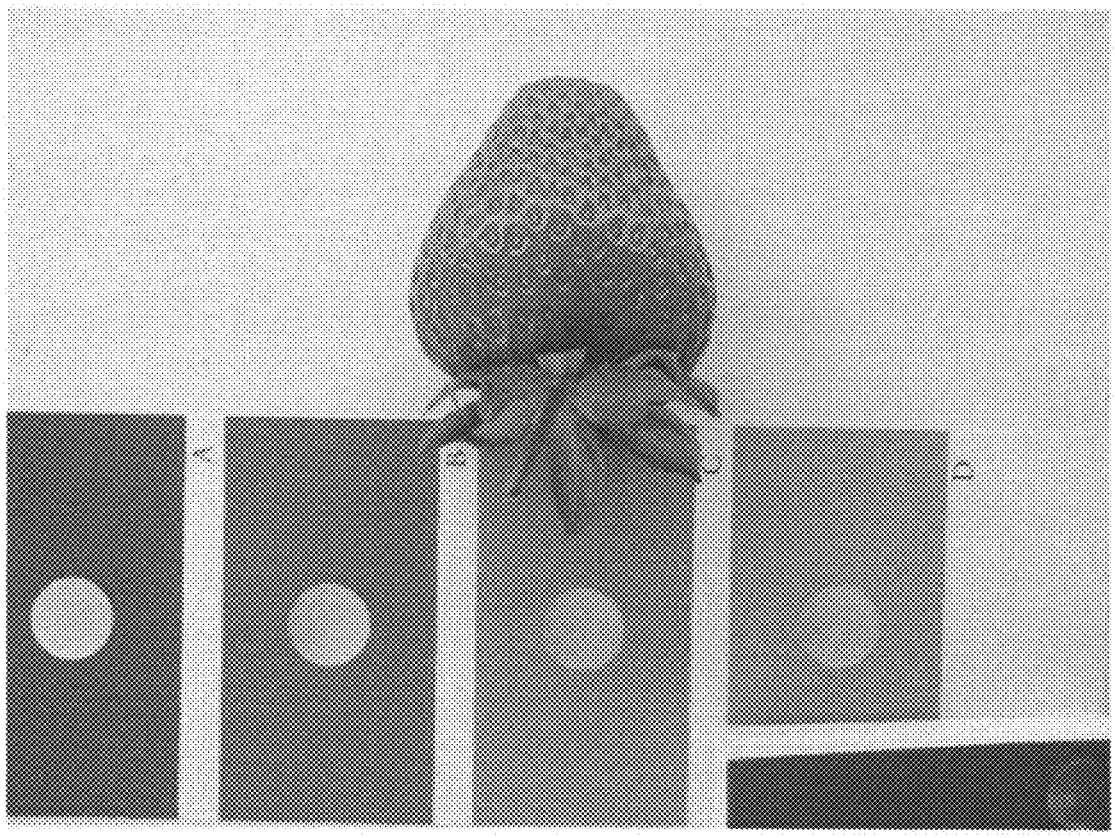

FIG. 14 Upper calyx surface color identification of a mature 'Viva Patricia' fruit using The 1995 Royal Horticultural Society Colour Chart (Yellow-Green 148C)

Figure 15:
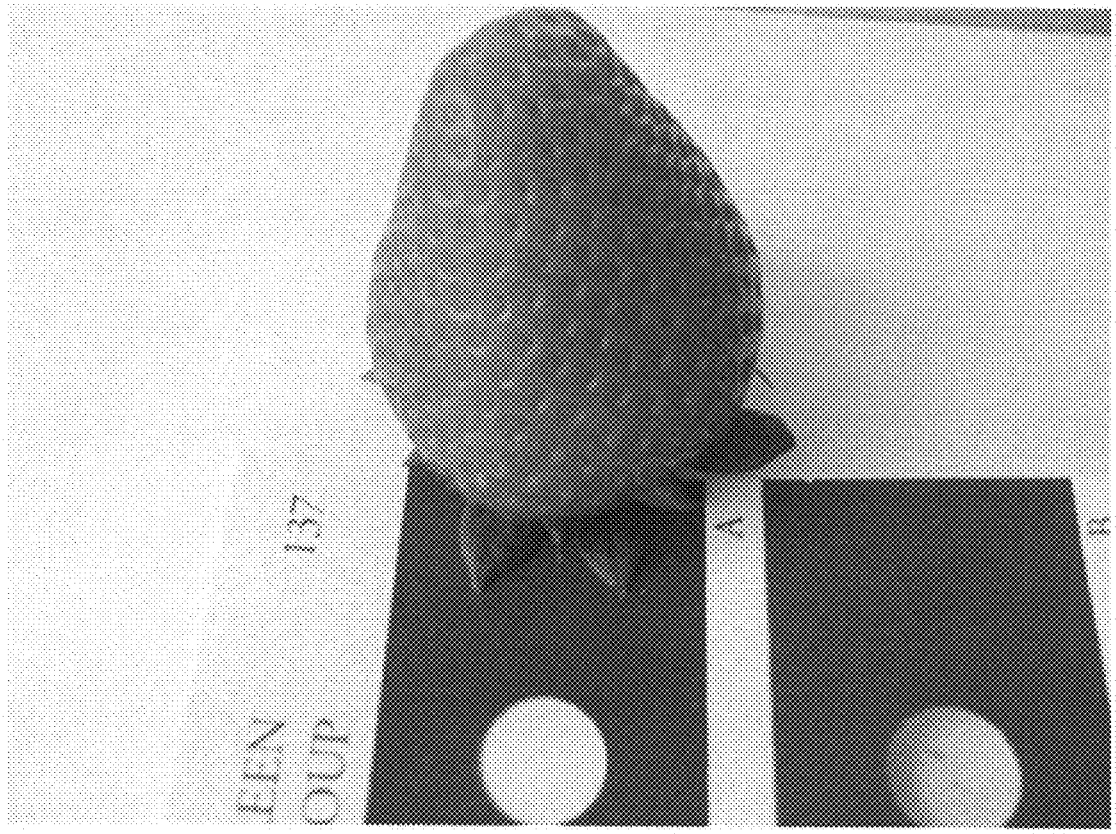

FIG. 15 Lower calyx surface color identification of a mature 'Viva Patricia' fruit using The 1995 Royal Horticultural Society Colour Chart (Green 137A)

Figure 16:
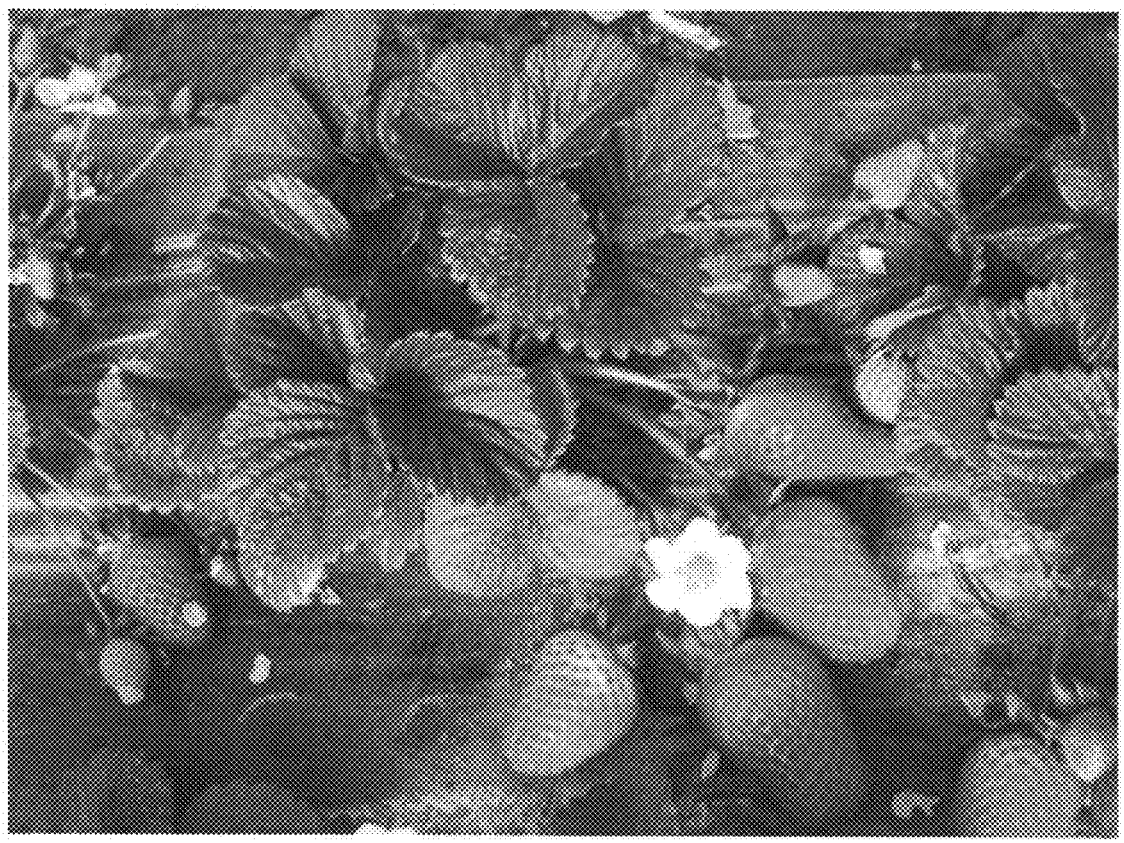

FIG. 16 Photo of cropping 'Viva Patricia' plant in early spring showing the simple flower and fruit trusses.

Figure 17:
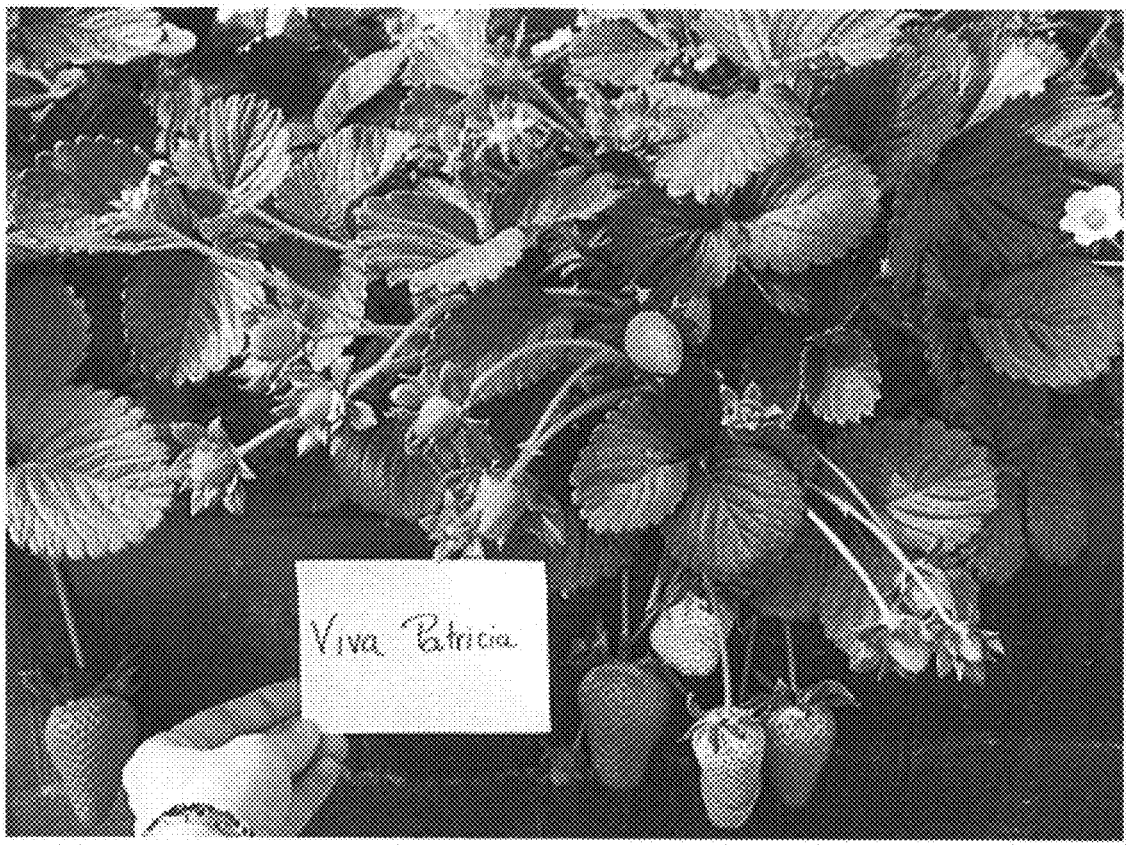

FIG. 17 Photo of a cropping 'Viva Patricia' plant in mid-season showing the leaves, flowers, and fruits visible at various developmental stages.

Figure 18:
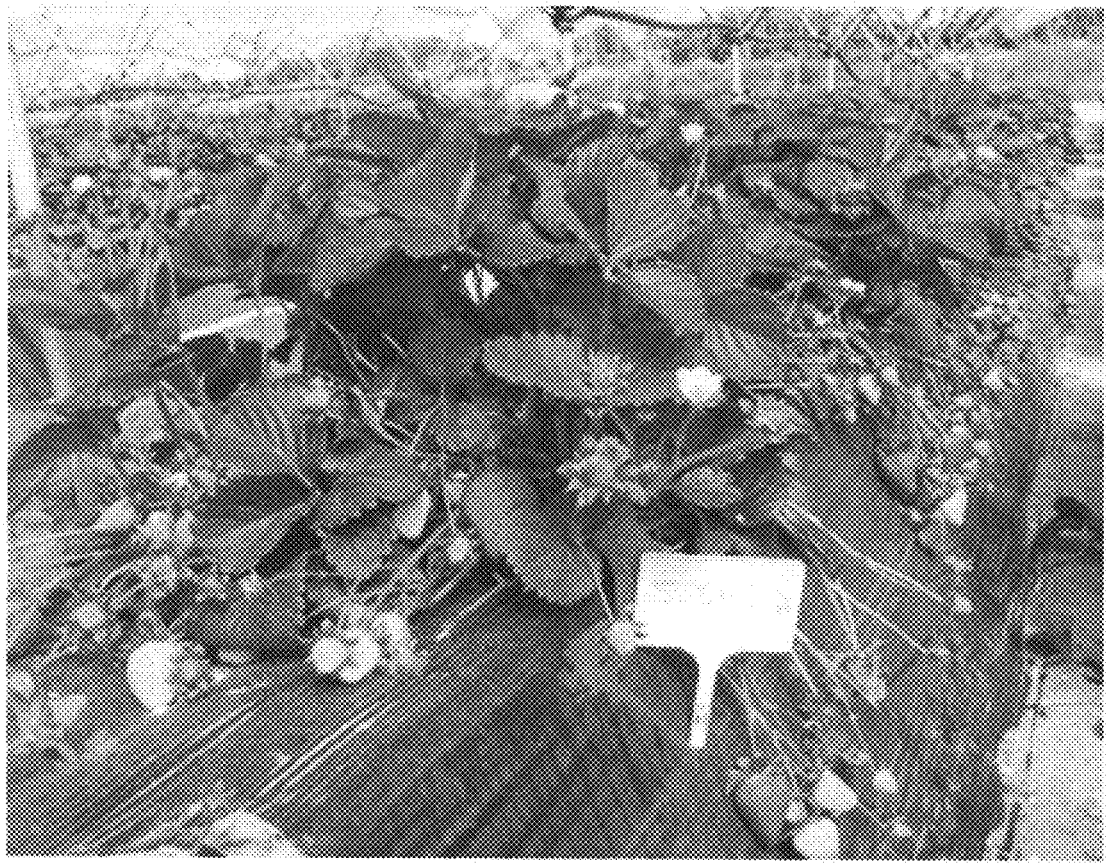

FIG. 18 Close shot of a typical mature 'Viva Patricia' plant towards the end of the cropping season.

DETAILED BOTANICAL DESCRIPTION OF THE NEW CULTIVAR

The following description of 'Viva Patricia', unless otherwise noted, is based on observations taken of plants and fruits grown in a trials field covered with polyethylene clad tunnels as part of an ongoing Mediterranean breeding program in a breeding field located in Cartaya, Spain.

The following description is in accordance with UPOV terminology and the color terminology used herein, unless otherwise indicate, is in accordance with The 1995 Royal Horticultural Society Colour Chart. The color descriptions and other phenotypical descriptions may deviate from the stated values and descriptions depending upon variation in environmental, seasonal, climatic, and cultural conditions.

Propagation

The new variety is principally propagated by way of stolons. Although propagation by stolons is presently preferred, other known methods of propagating strawberry plants may be used. Strawberry plants root well following transplanting.

Comparative Fruit Characteristics

The fruit characteristics of 'Viva Patricia' include, but are not limited to, the characteristics of the fruit itself, the fruit production, and the fruit quality. Fruit characteristics for 'Viva Patricia' were observed over four (4) seasons and the data was taken from the 2009 harvest season.

Table 1

Table 1 shows the average fruit yield, size, and Brix measurements of 'Viva Patricia' when compared against two standard varietes, 'Sabrosa' (U.S. Plant Pat. No. 16,558) and 'Camarosa' (U.S. Plant Pat. No. 8,708). The measurements of all three cultivars were taken in 2009 and subjected to the environmental and growing conditions as they existed in Cartaya, Spain at that time. Accordingly, all field records were taken from commercial plantings in Spain.

Fruit harvest started on 4 Mar. 2009 and continued through the spring until conclusion on 8 May 2009. All three cultivars were planted in mid October 2008.

| Cultivar | Average (Average total yield in grams per plant) | Average Brix |
|---|---|---|
| 'Viva Patricia' | 995.30 | 13.7 |
| 'Sabrosa' | 866.50 | 13.5 |
| 'Camarosa' | 1010.50 | 8.5 |

Table 2

Table 2 compares the fruit characteristics of 'Viva Patricia' berries with two standard varieties, 'Sabrosa' and 'Camarosa'. Measurements provided were taken from fully mature (ripe) primary fruits from the field in Cartaya, Spain in April 2009. Fruit width is measured across the widest part of the berry, typically, across the shoulders of the berry. The measurements of all three cultivars were taken in 2009 and subjected to the environmental and growing conditions as they existed in Cartaya, Spain at that time. Accordingly, all field records were taken from commercial plantings in Spain.

| Characteristic | 'Viva Patricia' | 'Sabrosa' | 'Camarosa' |
|---|---|---|---|
| Exterior Color | Red (RHS) 45A | Red (RHS) 43B | 7.5R 4/11 to 7.5R 3/6 (Munsell) |
| Internal Color | Orange-Red (RHS) 33A | N/A† | 7.5R 5/13 to 7.5R 4/11 (Munsell) |
| Achene Color | Yellow (RHS) 12A | Orange-Red (RHS) 33B to 33C | N/A* |
| Mature Fruit Length Mean (mm) | 64 | 62 | 56 |
| Mature Fruit Width Mean (mm) | 47 | 43 | 46 |
| Mature Fruit Length/Width Ratio | 1.4 | 1.4 | 1.2 |
| No. of Achenes per cm2 | 14/cm2/ primary berry | 13.2/cm2/ primary berry | 15.4/cm2/ primary berry |
| Achene Position | Slightly indented | Level with surface | Even |

†Color data for the comparative varieties, 'Sabrosa' and 'Camarosa', was collected from their respective Patents. In those instances where color determinations were not disclosed in the Patents, the term "not available" or "N/A" has been substituted for the actual color data.

Table 3

Table 3 compares the fruit quality characteristics of 'Viva Patricia' with the fruit quality characteristics of 'Sabrosa' and 'Camarosa.' Comparisons of fruit quality include, but are not limited to, flesh firmness, soluble solids (as measured by % Brix), and acidity. The measurements of all three cultivars were taken in 2009 and subjected to the environmental and growing conditions as they existed in Cartaya, Spain at that time. Accordingly, all field records were taken from commercial plantings in Spain.

| Characteristic | 'Viva Patricia' | 'Sabrosa' | 'Camarosa' |
|---|---|---|---|
| Fruit Skin Firmness | Very firm | Very firm | Firm |
| Flesh Firmness | Moderate firmness | Very firm | Very firm |
| Fruit Appearance | 5.0 | 5.0 | 4.0 |
| Fruit Aroma | Moderate aroma | Moderate aroma | Absence of aroma |
| Fruit Sweetness | Strong sweetness | Strong sweetness | Low sweetness |
| Soluble Solids | 13.7 | 13.5 | 8.5 |
| Acidity | Very low acidity | Medium acidity | Medium acidity |

Detailed fruit characteristics of 'Viva Patricia':

*Ratio of length to width.*—Longer than broad.

*Size.*—Large.

*Predominant shape.*—Conical.

*Aroma.*—Moderate.

*Differences in shape between primary and secondary fruit.*—Slight.

*Differences in shape between primary and tertiary fruit.*—Slight to moderate.

*Band without achenes.*—Narrow width.

*Color of mature fruit (ripe).*—Red group (Red 45A).

*Evenness of color.*—Very even.

*Glossiness.*—Very high.

*Achene position.*—Slightly indented.

*Attitude of the calyx segments.*—Level with berry shoulder.

*Calyx depth.*—15 mm average.

*Calyx surface texture.*—Smooth.

*Color of the upper (adaxial) surface of the calyx.*—Yellow-Green group (Yellow-Green 148C).

*Color of the lower (abaxial) surface of the calyx.*—Green group (Green 137A).

*Size of calyx in relation to fruit diameter.*—Medium.

*Number of sepals.*—Approximately 13.5.

*Firmness of skin.*—Very firm.

*Firmness of flesh.*—Moderate firmness.

*Color of flesh.*—Interior flesh coloration near the outside edges of the fruit surface approaches bright Orange-Red (33A) and the inner core approaches Orange-Red (35A).

*Hollow center.*—Moderately expressed in primary fruit and not expressed in secondary and tertiary fruit.

*Achene color.*—Generally bright yellow (Yellow 12A), however, when fully exposed to light, achenes are red (Red 39A) in color.

*Time of flowering (50% of plants at first flower).*—Mid-season.

*Time of ripening* (50% *of plants with first ripe fruit*).—Mid-season.

*Type of bearing.*—Short day (Mediterranean).

Comparative Plant Characteristics

Table 4

Table 4 is a comparison of the plant characteristics of 'Viva Patricia' with the plant characteristics of 'Sabrosa' and 'Camarosa' when the varieties were grown side-by-side in Cartaya, Spain. Comparisons of plant characteristics include differences in plant height, width, and breadth and based on measurements made on mature plants in mid-season. The measurements of all three cultivars were taken in 2009 and subjected to the environmental and growing conditions as they existed in Cartaya, Spain at that time. Accordingly, all field records were taken from commercial plantings in Spain.

| Characteristic | 'Viva Patricia' | 'Sabrosa' | 'Camarosa' |
|---|---|---|---|
| Plant Height Mean (mm) | 233 | 245 | 218 |
| Plant Width Mean (mm) | 391 | 348 | 306 |
| Plant Breadth Mean (mm) | 383 | 389 | 315 |

Detailed plant characteristics of 'Viva Patricia':

*Size.*—Medium to large.

*Habit.*—Vigorous with dense canopy.

Comparative Foliage Characteristics

Table 5

Table 5 compares the leaf characteristics of 'Viva Patricia' with the leaf characteristics of 'Sabrosa' and 'Camarosa.' Foliage characteristics are taken from a fully mature tri-foliate leaf in April 2009 in Cartaya, Spain. The measurements of all three cultivars were taken in 2009 and subjected to the environmental and growing conditions as they existed in Cartaya, Spain at that time. Accordingly, all field records were taken from commercial plantings in Spain

| Characteristic | 'Viva Patricia' | 'Sabrosa' | 'Camarosa' |
|---|---|---|---|
| Adaxial Surface Color | Green 137A (RHS) | Green near 137C to 137B (RHS) | 5GY 4/3 (Munsell) |
| Abaxial Surface Color | Green 138B (RHS) | Green near 138D to 138C (RHS) | 5GY 5/6 (Munsell) |
| Mid-tier Leaflet Length Mean (mm) | 85 | 85 | 82 |
| Mid-tier Leaflet Width Mean (mm) | 85.4 | 82 | 80 |
| Petiole Length Mean (mm) | 205 | 201 | 179 |
| Petiole Diameter (mm) | 5 | 4 | 4 |
| Petiole Color | Yellow-Green 144B (RHS) | Green near 138D (RHS) | N/A* |
| Petiolule Length Mean (mm) | 8 | 12 | 8 |
| Stipule Length Mean (mm) | 33.5 | 31 | 34 |
| Stipule Color | Red 47A (RHS) | Greyed Red near 179C to 179B | N/A* |
| Serrations per Leaf | 20 | 21 | 19 |
| Number of Leaflets/Leaf | 3 | 3 | 3 |

-continued

| Characteristic | 'Viva Patricia' | 'Sabrosa' | 'Camarosa' |
|---|---|---|---|
| Leaf Convexity | Flat to slightly concave | Slightly concave | Concave |

Detailed foliage characteristics of 'Viva Patricia':

*Color of adaxial surface.*—Green (137A).

*Color of abaxial surface.*—Green (138B).

*Shape in cross section.*—Flat to slightly concave.

*Blistering.*—Slight puckering/blistering that is visible on the mid-tier leaflets.

*Number of leaflets/leaf.*—Three.

*Mid-tier leaflet.*—Size — Medium. Shape — Almost round, slightly wider than long. Length/width ratio — Slightly wider than long. Shape of base — Obtuse. Shape of serrations — Slightly pointed to slightly rounded. Venation of leaflets — Pinnate.

*Petiole.*—Pubescence density — Slight. Petiole color — Yellow-Green (144B). Stipule color — Red Group (47A). Stipule length — 33.5 mm. Stipule width at base — 6 mm. Anthocyanin coloration of stipules — Very strong; Red Group (47A). Attitude of hairs — Hairs are perpendicular to the petiole. Size of bract leaflets — Small to medium. Frequency of bract leaflets — Bract leaflets are present on approximately 99% of flower trusses.

Comparative Flower and Inflorescence Characteristics

Table 6

Table 6 compares the inflorescence and secondary flower characteristics of 'Viva Patricia' with the inflorescence and secondary flower characteristics of 'Sabrosa' and 'Camarosa.' Inflorescence characteristics are taken from a fully mature plant in April 2009 in Cartaya, Spain. Flower characteristics are taken from a primary flower at full maturity. The measurements of all three cultivars were taken in 2009 and subjected to the environmental and growing conditions as they existed in Cartaya, Spain at that time. Accordingly, all field records were taken from commercial plantings in Spain.

| Characteristic | 'Viva Patricia' | 'Sabrosa' | 'Camarosa' |
|---|---|---|---|
| Fruiting Truss Length Mean (mm) | 313 | 281 | 239 |
| Corolla Diameter Mean (mm) | 38 | 41 | 37 |
| Calyx Diameter Mean (mm) | 45.9 | 51 | 52 |
| Petal Length Mean (mm) | 15.9 | 12 | 13 |
| Petal Width Mean (mm) | 18 | 14 | 13 |
| Petal Length/Width Ratio | 0.88 | 0.85 | 1.0 |
| Petals per Flower Mean | 7 | 6 | 6 |

Detailed inflorescence characteristics of 'Viva Patricia':

*Position relative to foliage.*—Some internal, mostly even and some exposed.

*Fruiting truss length.*—Medium to long.

Detailed flower characteristics of 'Viva Patricia':

*Color.*—White.

*Size.*—Medium to large.

*Size of calyx relative to corolla.*—Larger.

*Petal length to width ratio.*—Wider than long.

*Petal shape.*—Nearly round having an obtuse base and apex, slightly overlapping.

*Petal margins.*—Entire.

Pest Reactions

Reactions to major pest and disease are not fully tested. Some field evidence suggests that the plants of 'Viva Patricia' are susceptible to *Phytophtora cactorum.* The susceptibility of the new cultivar to any of the Mediterranean virus complexes has not been determined.

COMPARISON WITH KNOWN VARIETIES

The variety which is believed to most closely resemble 'Viva Patricia' is 'Sabrosa' (U.S. Plant Pat. No. 16,558). When compared to similar cultivars 'Sabrosa' and 'Camarosa', 'Viva Patricia' differs by the following characteristics.

'Viva Patricia' is a typical short day (Mediterranean) strawberry cultivar, being slightly earlier in season than 'Sabrosa' (U.S. Plant Pat. No. 16,558) when 'Sabrosa' was subjected to the growing conditions of Spain. The production pattern for 'Viva Patricia', when grown in Spain, is more consistent than 'Sabrosa' which tends to produce peaks and troughs.

Following a comparison of Viva Patricia' to 'Camarosa' (U.S. Plant Pat. No. 8,708) after subjecting 'Camarosa' to the growing conditions of Spain, it was determined that 'Viva Patricia' has an overall fruit shape and uniformity of shape far superior to that of 'Camarosa.' Viva Patricia' produces a fruit that has a firm skin and is juicier and paler in color than either of the 'Sabrosa' or 'Camarosa' varieties. Further, the fruit of 'Viva Patricia' has Brix levels averaging 13.7% for twelve (12) consecutive weeks. Accordingly, 'Viva Patricia' is significantly better flavored and sweeter than either of the 'Camarosa' or 'Sabrosa' varieties. Finally, 'Viva Patricia' possesses a refreshing and pleasant aroma not found in the 'Camarosa' variety.

'Viva Patricia' plants exhibit a slightly more vigorous growth habit than either 'Sabrosa' or 'Camarosa' when the comparative cultivars are grown in Spain. 'Viva Patricia' plants produce more crown numbers per plant and a greater number of leaves than either of the 'Sabrosa' or 'Camarosa' varieties. Further still, 'Viva Patricia' produces leaves that are larger than the leaves produced by either of the comparative cultivars, 'Sabrosa' or 'Camarosa.' 'Viva Patricia' produces leaflets which are generally round and almost as wide as long.

The petiole and petiolule lengths of 'Viva Patricia' are greater than that of 'Sabrosa' or 'Camarosa', and the petiole pubescence density of 'Viva Patricia' is significantly less when compared to 'Sabrosa', which has very heavy pubescence. Some hair is present on 'Viva Patricia' at the base of the petiole and close to the stipules. The petiolule pubescence of 'Viva Patricia' is moderate, but still significantly less than that of 'Sabrosa.'

The leaflets of 'Viva Patricia' typically possess a slightly round (obtuse) base and tip. The serrations express slightly pointed to slightly rounded tips with the leaflets of 'Viva Patricia' plants possessing a slightly smaller number of serrations per leaf than that of 'Sabrosa' and a slightly higher number of serrations per leaf than that of 'Camarosa.' Leaflets of 'Viva Patricia' exhibit slight puckering/blistering that is visible on the mid-tier leaflets.

'Viva Patricia' flower trusses tend to grow within the foliage and do not protrude above the leaf canopy. Instead, flowers tend to open at the canopy level, however, when loaded with fruit, the fruit trusses tend to protrude to the sides of the plant. The presence of a bract, which progresses into a typical leaflet as the truss matures and the fruit develops, can be seen on 99% of the flower trusses from an early developmental stage. Generally, there are more flowers and fruits per truss than either of the 'Sabrosa' or 'Camarosa' varieties.

The flowers of 'Viva Patricia' are slightly larger and stronger than those of 'Sabrosa' and generally are greater in number. The primary flowers of 'Viva Patricia' are generally larger than those of 'Sabrosa.' Petal numbers of 'Viva Patricia' are similar to 'Sabrosa', however, the petals of 'Viva Patricia' have an entire margin and the obtuse base and apex and are slightly overlapping. Additionally, 'Viva Patricia' exhibits broader and shorter petals than 'Sabrosa.' The calyx of 'Viva Patricia' is similar to that of 'Sabrosa', however, the calyxes of the primary fruit for 'Viva Patricia' are very simple having one (1) or two (2) indentations. The calyxes on the secondary and tertiary fruit of 'Viva Patricia', however, are completely devoid of serrations. The calyxes of 'Viva Patricia' are spreading and slightly recurving.

The berries of 'Viva Patricia' are medium to large in size with a shape that is predominantly conical with rounded shoulders. 'Viva Patricia' berries are glossier and paler than those of 'Sabrosa.' Specifically, the external and internal fruit color of 'Viva Patricia' is brighter and is substantially lighter than either of the 'Sabrosa' or 'Camarosa' varieties. During the cropping season, the fruit of 'Viva Patricia' retains its bright red color and appears to be unaffected by the higher seasonal temperatures. 'Sabrosa' and 'Camarosa' fruit, however, have darker skin colorations.

The achenes of 'Viva Patricia' berries are characterized as being generally even to slightly indented into the surface of the fruit, whereas 'Camarosa' has even achenes. 'Viva Patricia' berries generally contain fewer achenes than those of 'Camarosa' and slightly more than that of 'Sabrosa.'

The fruit of 'Viva Patricia' is significantly sweeter and juicier than that of 'Camarosa' throughout the cropping season and provides a very pleasant combination of flavor, sugar and low acid levels. The berry skin of 'Viva Patricia' is firmer than that of 'Camarosa' and does not bruise readily during rubbing. 'Viva Patricia' fruit is more aromatic than that of 'Camarosa' and possesses a very pleasant scent. The fruit flesh of Viva Patricia is less firm than those of the comparative cultivars, 'Sabrosa' and 'Camarosa', providing for a less crunchy texture and a more pleasant eating experience. 'Viva Patricia' retains a very good fruit quality throughout the cropping season and is stable in its essential characteristics, i.e. fruit size, shape, quality, color, firmness, Brix levels, and plant habit.

Flower initiation and flower expression of 'Viva Patricia' are generally linear; however, variation in the climate might cause slight fluctuations. Termination of flowering is temperature and day-length dependent.

Commercial ratings for 'Viva Patricia' are similar to those of 'Sabrosa' but are superior to those of 'Camarosa.' Specifically, the fruits of 'Viva Patricia' have a significantly improved shelf-life, a superior firmness, an outstanding flavor, and a higher level of sugar than those of 'Camarosa.'

When grown in Spain under appropriate management, the cropping season for 'Viva Patricia' starts in February, slightly earlier than that of 'Sabrosa', and continues until the end of May. Subject to these growth conditions, 'Viva Patricia' has a more uniform fruit shape and size and produces a substantially greater class 1 yield per plant throughout the cropping season than 'Camarosa.'

What is claimed is:

1. A new and distinct cultivar of strawberry plant named 'Viva Patricia' substantially as herein described and illustrated by the characteristics set forth above.

* * * * *